United States Patent
Gilham et al.

(10) Patent No.: US 12,173,316 B2
(45) Date of Patent: Dec. 24, 2024

(54) COMPOSITIONS AND METHODS FOR IMPROVING PERSISTENCE OF CELLS FOR ADOPTIVE TRANSFER

(71) Applicant: CELYAD S.A, Mont-Saint-Guibert (BE)

(72) Inventors: David Gilham, Mont-Saint-Guibert (BE); Simon Bornschein, Mont-Saint-Guibert (BE); Susanna Raitano, Mont-Saint-Guibert (BE)

(73) Assignee: CELYAD S.A, Mont-Saint-Guibert (BE)

( * ) Notice: Subject to any disclaimer, the term of this patent is extended or adjusted under 35 U.S.C. 154(b) by 944 days.

(21) Appl. No.: 16/769,634

(22) PCT Filed: Dec. 5, 2018

(86) PCT No.: PCT/EP2018/083701
§ 371 (c)(1),
(2) Date: Jun. 4, 2020

(87) PCT Pub. No.: WO2019/110693
PCT Pub. Date: Jun. 13, 2019

(65) Prior Publication Data
US 2021/0171907 A1    Jun. 10, 2021

(30) Foreign Application Priority Data
Dec. 5, 2017 (EP) ..................... 17205564

(51) Int. Cl.
| | | |
|---|---|---|
| C12N 5/0783 | (2010.01) | |
| A61K 35/17 | (2015.01) | |
| A61P 35/00 | (2006.01) | |
| C07K 14/705 | (2006.01) | |
| C12N 15/113 | (2010.01) | |

(52) U.S. Cl.
CPC ............ *C12N 5/0636* (2013.01); *A61K 35/17* (2013.01); *A61P 35/00* (2018.01); *C07K 14/7056* (2013.01); *C12N 15/1138* (2013.01); *C12N 2310/14* (2013.01); *C12N 2310/531* (2013.01); *C12N 2501/515* (2013.01)

(58) Field of Classification Search
None
See application file for complete search history.

(56) References Cited

U.S. PATENT DOCUMENTS

| | | |
|---|---|---|
| 2008/0242610 A1 | 10/2008 | Wagner |
| 2012/0020938 A1 | 1/2012 | Hyde et al. |
| 2014/0356321 A1 | 12/2014 | Cheung et al. |
| 2017/0016025 A1 | 1/2017 | Poirot et al. |

FOREIGN PATENT DOCUMENTS

| | | | |
|---|---|---|---|
| JP | 2017-508468 | 3/2017 | |
| JP | 2017532950 | 11/2017 | |
| WO | 2014/117121 | 7/2014 | |
| WO | 2015136001 | 9/2015 | |
| WO | 2016011210 | 1/2016 | |
| WO | WO-2016011210 A2 * | 1/2016 | ............ A61K 35/17 |
| WO | 2016094679 | 6/2016 | |
| WO | 2016/154585 | 9/2016 | |

OTHER PUBLICATIONS

Molinero, 2002, J. Leuk. Biol. vol. 71: 791-797.*
Huang, 2013, Hepatology, vol. 57: 277-288.*
Song, De-Gang et al. "Chimeric NKG2D CAR-expressing T cell-mediated attack of human ovarian cancer is enhanced by histone deacetylase inhibition." Human gene therapy vol. 24,3 (2013): 295-305. doi:10.1089/hum.2012.143.
Zhang, Tong et al. "Generation of antitumor responses by genetic modification of primary human T cells with a chimeric NKG2D receptor." Cancer research vol. 66, 11 (2006): 5927-33. doi:10.1158/0008-5472.CAN-06-0130.

* cited by examiner

*Primary Examiner* — Amy E Juedes
(74) *Attorney, Agent, or Firm* — Robin L. Teskin; Baker, Donelson, Bearman, Caldwell & Berkowitz PC

(57) ABSTRACT

The present application relates to the field of immunotherapy, more particularly to the manufacture of cells for adoptive cell therapy. Provided herein are compositions and methods for improving in vivo persistence of cells intended for adoptive transfer. This is achieved by making the cells less vulnerable to clearance caused by NK cells of the subject receiving the adoptive cell therapy.

14 Claims, 5 Drawing Sheets
Specification includes a Sequence Listing.

SEQUENCE LISTING

<160> NUMBER OF SEQ ID NOS: 42

<210> SEQ ID NO 1
<211> LENGTH: 19
<212> TYPE: DNA
<213> ORGANISM: Artificial Sequence
<220> FEATURE:
<223> OTHER INFORMATION: Target sequence

<400> SEQUENCE: 1
caggatgggg tatctttga                                                19

<210> SEQ ID NO 2
<211> LENGTH: 19
<212> TYPE: DNA
<213> ORGANISM: Artificial Sequence
<220> FEATURE:
<223> OTHER INFORMATION: Target sequence

<400> SEQUENCE: 2
ccaggagatt agggtctgt                                                19

<210> SEQ ID NO 3
<211> LENGTH: 19
<212> TYPE: DNA
<213> ORGANISM: Artificial Sequence
<220> FEATURE:
<223> OTHER INFORMATION: Target sequence

<400> SEQUENCE: 3
tgatgggaat ggaacctac                                                19

<210> SEQ ID NO 4
<211> LENGTH: 19
<212> TYPE: DNA
<213> ORGANISM: Artificial Sequence
<220> FEATURE:
<223> OTHER INFORMATION: Target sequence

<400> SEQUENCE: 4
aagaccaaga cacactatc                                                19

<210> SEQ ID NO 5
<211> LENGTH: 19
<212> TYPE: DNA
<213> ORGANISM: Artificial Sequence
<220> FEATURE:
<223> OTHER INFORMATION: Target sequence

<400> SEQUENCE: 5
atgtcctgcc tgatgggaa                                                19

<210> SEQ ID NO 6
<211> LENGTH: 19
<212> TYPE: DNA
<213> ORGANISM: Artificial Sequence
<220> FEATURE:
<223> OTHER INFORMATION: Target sequence

<400> SEQUENCE: 6
ggtcctggat caacaccca                                                19

<210> SEQ ID NO 7
<211> LENGTH: 19
<212> TYPE: DNA
<213> ORGANISM: Artificial Sequence

```
<220> FEATURE:
<223> OTHER INFORMATION: Target sequence

<400> SEQUENCE: 7
atggtcagcc cttcctgcg                                                19

<210> SEQ ID NO 8
<211> LENGTH: 19
<212> TYPE: DNA
<213> ORGANISM: Artificial Sequence
<220> FEATURE:
<223> OTHER INFORMATION: Target sequence

<400> SEQUENCE: 8
ggaacacagc gggaatcac                                                19

<210> SEQ ID NO 9
<211> LENGTH: 19
<212> TYPE: DNA
<213> ORGANISM: Artificial Sequence
<220> FEATURE:
<223> OTHER INFORMATION: Target sequence

<400> SEQUENCE: 9
tctgtgcagt cagggtttc                                                19

<210> SEQ ID NO 10
<211> LENGTH: 19
<212> TYPE: DNA
<213> ORGANISM: Artificial Sequence
<220> FEATURE:
<223> OTHER INFORMATION: Target sequence

<400> SEQUENCE: 10
gaatggaacc taccagacc                                                19

<210> SEQ ID NO 11
<211> LENGTH: 60
<212> TYPE: DNA
<213> ORGANISM: Artificial Sequence
<220> FEATURE:
<223> OTHER INFORMATION: Sense Design sequence

<400> SEQUENCE: 11
ggcttcaaag atccccatc ctggggattg agttttgaac tccaggatgc ggtatctttg    60

<210> SEQ ID NO 12
<211> LENGTH: 60
<212> TYPE: DNA
<213> ORGANISM: Artificial Sequence
<220> FEATURE:
<223> OTHER INFORMATION: Sense Design

<400> SEQUENCE: 12
ggcttcagac cctaatctcc tggggattg agttttgaac tcccaggagt ttagggtctg    60

<210> SEQ ID NO 13
<211> LENGTH: 60
<212> TYPE: DNA
<213> ORGANISM: Artificial Sequence
<220> FEATURE:
<223> OTHER INFORMATION: Sense Design

<400> SEQUENCE: 13
ggctttaggt tccattccca tcagggattg agttttgaac tctgatgggt atggaaccta   60
```

```
<210> SEQ ID NO 14
<211> LENGTH: 60
<212> TYPE: DNA
<213> ORGANISM: Artificial Sequence
<220> FEATURE:
<223> OTHER INFORMATION: Sense Design

<400> SEQUENCE: 14
ggcttatagt gtgtcttggt cttgggattg agttttgaac tcaagaccat gacacactat    60

<210> SEQ ID NO 15
<211> LENGTH: 60
<212> TYPE: DNA
<213> ORGANISM: Artificial Sequence
<220> FEATURE:
<223> OTHER INFORMATION: Sense Design sequence

<400> SEQUENCE: 15
ggctttccca tcaggcagga catgggattg agttttgaac tcatgtcctc cctgatggga    60

<210> SEQ ID NO 16
<211> LENGTH: 60
<212> TYPE: DNA
<213> ORGANISM: Artificial Sequence
<220> FEATURE:
<223> OTHER INFORMATION: Sense Design sequence

<400> SEQUENCE: 16
ggcttgggtg ttgatccagg accgggattg agttttgaac tcggtcctgc atcaacaccc    60

<210> SEQ ID NO 17
<211> LENGTH: 60
<212> TYPE: DNA
<213> ORGANISM: Artificial Sequence
<220> FEATURE:
<223> OTHER INFORMATION: Sense Design

<400> SEQUENCE: 17
ggcttgcagg aagggctgac catgggattg agttttgaac tcatggtcac cccttcctgc    60

<210> SEQ ID NO 18
<211> LENGTH: 60
<212> TYPE: DNA
<213> ORGANISM: Artificial Sequence
<220> FEATURE:
<223> OTHER INFORMATION: Sense Design sequence

<400> SEQUENCE: 18
ggctttgatt cccgctgtgt tccgggattg agttttgaac tcggaacact gcgggaatca    60

<210> SEQ ID NO 19
<211> LENGTH: 60
<212> TYPE: DNA
<213> ORGANISM: Artificial Sequence
<220> FEATURE:
<223> OTHER INFORMATION: Sense Design sequence

<400> SEQUENCE: 19
ggcttaaacc ctgactgcac agagggattg agttttgaac tctctgtgct gtcagggttt    60

<210> SEQ ID NO 20
<211> LENGTH: 60
<212> TYPE: DNA
<213> ORGANISM: Artificial Sequence
<220> FEATURE:
<223> OTHER INFORMATION: Sense Design
```

<400> SEQUENCE: 20
ggcttgtctg gtaggttcca ttcgggattg agttttgaac tcgaatggat cctaccagac        60

<210> SEQ ID NO 21
<211> LENGTH: 60
<212> TYPE: DNA
<213> ORGANISM: Artificial Sequence
<220> FEATURE:
<223> OTHER INFORMATION: Antisense Design sequence

<400> SEQUENCE: 21
actccaaaga taccgcatcc tggagttcaa aactcaatcc ccaggatggg gtatctttga        60

<210> SEQ ID NO 22
<211> LENGTH: 60
<212> TYPE: DNA
<213> ORGANISM: Artificial Sequence
<220> FEATURE:
<223> OTHER INFORMATION: Antisense Design sequence

<400> SEQUENCE: 22
actccagacc ctaaactcct gggagttcaa aactcaatcc cccaggagat tagggtctga        60

<210> SEQ ID NO 23
<211> LENGTH: 60
<212> TYPE: DNA
<213> ORGANISM: Artificial Sequence
<220> FEATURE:
<223> OTHER INFORMATION: Antisense Design sequence

<400> SEQUENCE: 23
actctaggtt ccatacccat cagagttcaa aactcaatcc ctgatgggaa tggaacctaa        60

<210> SEQ ID NO 24
<211> LENGTH: 60
<212> TYPE: DNA
<213> ORGANISM: Artificial Sequence
<220> FEATURE:
<223> OTHER INFORMATION: Antisense Design sequence

<400> SEQUENCE: 24
actcatagtg tgtcatggtc ttgagttcaa aactcaatcc caagaccaag acacactata        60

<210> SEQ ID NO 25
<211> LENGTH: 60
<212> TYPE: DNA
<213> ORGANISM: Artificial Sequence
<220> FEATURE:
<223> OTHER INFORMATION: Antisense Design sequence

<400> SEQUENCE: 25
actctcccat cagggaggac atgagttcaa aactcaatcc catgtcctgc ctgatgggaa        60

<210> SEQ ID NO 26
<211> LENGTH: 60
<212> TYPE: DNA
<213> ORGANISM: Artificial Sequence
<220> FEATURE:
<223> OTHER INFORMATION: Antisense Design sequence

<400> SEQUENCE: 26
actcgggtgt tgatgcagga ccgagttcaa aactcaatcc cggtcctgga tcaacaccca        60

<210> SEQ ID NO 27

```
<211> LENGTH: 60
<212> TYPE: DNA
<213> ORGANISM: Artificial Sequence
<220> FEATURE:
<223> OTHER INFORMATION: Antisense Design sequence

<400> SEQUENCE: 27
actcgcagga agggtgacc atgagttcaa aactcaatcc catggtcagc ccttcctgca    60

<210> SEQ ID NO 28
<211> LENGTH: 60
<212> TYPE: DNA
<213> ORGANISM: Artificial Sequence
<220> FEATURE:
<223> OTHER INFORMATION: Antisense Design sequence

<400> SEQUENCE: 28
actctgattc ccgcagtgtt ccgagttcaa aactcaatcc cggaacacag cgggaatcaa    60

<210> SEQ ID NO 29
<211> LENGTH: 60
<212> TYPE: DNA
<213> ORGANISM: Artificial Sequence
<220> FEATURE:
<223> OTHER INFORMATION: Antisense Design sequence

<400> SEQUENCE: 29
actcaaaccc tgacagcaca gagagttcaa aactcaatcc ctctgtgcag tcagggttta    60

<210> SEQ ID NO 30
<211> LENGTH: 60
<212> TYPE: DNA
<213> ORGANISM: Artificial Sequence
<220> FEATURE:
<223> OTHER INFORMATION: Antisense Design sequence

<400> SEQUENCE: 30
actcgtctgg taggatccat tcgagttcaa aactcaatcc cgaatggaac ctaccagaca    60

<210> SEQ ID NO 31
<211> LENGTH: 20
<212> TYPE: DNA
<213> ORGANISM: Artificial Sequence
<220> FEATURE:
<223> OTHER INFORMATION: MICA-B-1

<400> SEQUENCE: 31
gtctgagctc tggaggactg                                                20

<210> SEQ ID NO 32
<211> LENGTH: 20
<212> TYPE: DNA
<213> ORGANISM: Artificial Sequence
<220> FEATURE:
<223> OTHER INFORMATION: MICA-B-2

<400> SEQUENCE: 32
acattcacca tgggggggcac                                               20

<210> SEQ ID NO 33
<211> LENGTH: 20
<212> TYPE: DNA
<213> ORGANISM: Artificial Sequence
<220> FEATURE:
<223> OTHER INFORMATION: MICA-B-3

<400> SEQUENCE: 33
``` agataccccca tcctgacgcc                                                20

<210> SEQ ID NO 34
<211> LENGTH: 20
<212> TYPE: DNA
<213> ORGANISM: Artificial Sequence
<220> FEATURE:
<223> OTHER INFORMATION: MICA-B-4

<400> SEQUENCE: 34
cacggtgatg ttgccctctg                                                 20

<210> SEQ ID NO 35
<211> LENGTH: 20
<212> TYPE: DNA
<213> ORGANISM: Artificial Sequence
<220> FEATURE:
<223> OTHER INFORMATION: MICA-B-5

<400> SEQUENCE: 35
gctcttcctc tcccaaaacc                                                 20

<210> SEQ ID NO 36
<211> LENGTH: 20
<212> TYPE: DNA
<213> ORGANISM: Artificial Sequence
<220> FEATURE:
<223> OTHER INFORMATION: MICA-B-6

<400> SEQUENCE: 36
ccccatcgta gtagaaatgc                                                 20

<210> SEQ ID NO 37
<211> LENGTH: 20
<212> TYPE: DNA
<213> ORGANISM: Artificial Sequence
<220> FEATURE:
<223> OTHER INFORMATION: MICA-B-7

<400> SEQUENCE: 37
gggcttccag cttctatccc                                                 20

<210> SEQ ID NO 38
<211> LENGTH: 20
<212> TYPE: DNA
<213> ORGANISM: Artificial Sequence
<220> FEATURE:
<223> OTHER INFORMATION: MICA-B-8

<400> SEQUENCE: 38 tgggggatg tcctgcctga                                                  20

<210> SEQ ID NO 39
<211> LENGTH: 20
<212> TYPE: DNA
<213> ORGANISM: Artificial Sequence
<220> FEATURE:
<223> OTHER INFORMATION: MICB-9

<400> SEQUENCE: 39
ctatgaacgt cacaaatttc                                                 20

<210> SEQ ID NO 40
<211> LENGTH: 20
<212> TYPE: DNA

```
<213> ORGANISM: Artificial Sequence
<220> FEATURE:
<223> OTHER INFORMATION: MICA-B-10

<400> SEQUENCE: 40
cggggccatg gggctgggcc                                               20

<210> SEQ ID NO 41
<211> LENGTH: 20
<212> TYPE: DNA
<213> ORGANISM: Artificial Sequence
<220> FEATURE:
<223> OTHER INFORMATION: MICA-B-11

<400> SEQUENCE: 41
catatcaagg accagaaaga                                               20

<210> SEQ ID NO 42
<211> LENGTH: 20
<212> TYPE: DNA
<213> ORGANISM: Artificial Sequence
<220> FEATURE:
<223> OTHER INFORMATION: MICA-B-12

<400> SEQUENCE: 42
atagtgtgtc ttggtcttca                                               20
```

COMPOSITIONS AND METHODS FOR IMPROVING PERSISTENCE OF CELLS FOR ADOPTIVE TRANSFER

CROSS-REFERENCE TO RELATED APPLICATIONS

This application is a U.S. National Phase Application of Int'l Appl. No. PCT/EP2018/083701, filed Dec. 5, 2018, which claims priority to Int'l Appl No. EP 17205564.2, filed Dec. 5, 2017, each of which is incorporated herein by reference.

SEQUENCE DISCLOSURE

This application includes as part of its disclosure a biological sequence listing, contained in a file named "1483070001601.txt" having a size of 8,241 bytes, which was created on Jul. 27, 2023, which is hereby incorporated by reference in its entirety.

FIELD OF THE INVENTION

The present application relates to the field of immunotherapy, more particularly to the manufacture of cells for adoptive cell therapy. Provided herein are compositions and methods for improving in vivo persistence of cells intended for adoptive transfer. This is achieved by making the cells less vulnerable to clearance caused by NK cells of the subject receiving h be adoptive cell therapy.

BACKGROUND

Adoptive cellular therapy or adoptive cell transfer (ACT) is becoming an ever more important treatment paradigm, particularly in the treatment of cancer. ACT refers to the transfer of cells, most typically immune cells, into a patient. These cells may have originated from the patient (autologous therapy) or from another individual (allogeneic therapy). The goal of the therapy is to improve immune functionality and characteristics, and in cancer immunotherapy, to raise an immune response against the cancer. Although T cells are most often used for ACT, it is also applied using other immune cell types such as NK cells, lymphocytes (e.g. tumor-infiltrating lymphocytes (TILs)), dendritic cells and myeloid cells.

Ideally, the cells that are infused in the subject (or reinfused in case of autologous therapy) receiving the ACT will expand and persist in the subject. To this end, lymphodepletion is often used as neoadjuvant therapy, to ensure there are no competing immune cells to repopulate the immune cell space. This is especially important for allogeneic therapy: as is the case with transplants, an immune response may be raised against non-self infused cells, both by the adaptive and the innate immune system. Sometimes myeloablation, high-dose chemotherapy that kills cells in the bone marrow, is also used. However, lymphodepletion or myeloablation are quite drastic measures that often result in severe side effects because of their effect on the immune system. Nevertheless, in current treatment paradigms they are always included to avoid a host versus graft response. Such response even happens in autologous therapy: whereas the modified immune cells are recognized as self by the adaptive immune system, they can still be attacked by the innate immune system because of the presence of induced self antigens. These are markers of 'abnormal' self, the expression of which is induced in stress conditions. Unfortunately, it appears the transduction and culture of patient cells to make them suitable for adoptive cell transfer also increases the presence of induced self antigens.

Accordingly, it would be advantageous to prevent or reduce the response of the innate immune system against infused ACT cells, as this would increase the persistence of the ACT cells in vivo and increase the benefits of the therapy. Ideally, this would lead to reduced need for lymphodepletion or myeloablative therapy, so that patients receiving ACT suffer less from side effects as well.

SUMMARY

It is an object of the invention to provide immune cells for adoptive cell transfer with increased in vivo persistence. This objective is achieved by reducing the innate immune response to these cells, particularly the innate immune response involved in recognizing induced-self antigens. A particularly well-known receptor involved in recognition of induced-self antigens is NKG2D. It was found that inactivation of one or more of the NKG2D ligands in immune cells intended for ACT at least partially masks these cells for the NK-mediated immune response. This results in reduced killing of the ACT cells and prolonged persistence in vivo.

Accordingly, engineered immune cells are provided that contain an exogenous nucleic acid molecule and at least one of:
  One or more endogenous genes encoding a NKG2D ligand that have been engineered to be inactivated;
  One or more inhibitors directed against one or more NKG2D ligands.

According to specific embodiments, the NKG2D ligands are selected from: MICA, MICB, ULBP1, ULBP2, ULBP3, ULBP4, ULBP5 and ULBP6. According to further specific embodiments, the NKG2D ligands are one or both selected from MICA and MICB.

According to particular embodiments, the one or more inhibitors are selected from RNA inhibitors, antibodies and peptide inhibitors. According to other particular embodiments, the genes that have been engineered to be inactivated are inactivated using Crispr/CAS, TALEN, ZFN, Meganucleases or MegaTAL technology.

According to further specific embodiments, the exogenous nucleic acid molecule encodes a chimeric antigen receptor or a TCR.

According to further particular embodiments, the chimeric antigen receptor is a NKG2D CAR.

According to a further aspect, methods are provided of rendering an immune cell less sensitive to clearance by NK cells comprising the inhibition of one or more NKG2D ligands in the immune cell.

According to particular embodiments, the immune cell further comprises an exogenous nucleic acid molecule. According to yet further particular embodiments, the exogenous nucleic acid molecule encodes a chimeric antigen receptor or a TCR.

According to specific embodiments, the inhibition of one or more NKG2D ligands is through genetic inactivation of one or more NKG2D ligands (e.g. using Crispr/CAS, TALEN, ZFN, Meganucleases or MegaTAL technology) or by administering one or more NKG2D ligand inhibitors (e.g. a RNA inhibitor, an antibody or a peptide inhibitor). According to further particular embodiments, the NKG2D ligand inhibitor is shRNA against one or more NKG2D ligands. According to specific embodiments, the NKG2D ligand inhibitor is shRNA against MICA and/or MICB.

Of note, the shRNA can be administered as such, or can be part of a viral vector (e.g. a retro- or lentiviral vector). In such cases, the one or more inhibitors directed against one or more NKG2D ligands are typically provided as an exogenous nucleic acid to be introduced in the engineered immune cell.

According to specific embodiments, the inhibition of NKG2D ligands (i.e. the engineering to inactivate the genes, or the addition of one or more inhibitors) is performed during manufacturing of said cells in vitro or ex vivo. The manufacturing of these cells does not involve the administration step.

According to yet a further aspect, the engineered immune cells or the compositions described herein are provided for use as a medicament. They are particularly suited for use in the treatment of cancer.

This is equivalent as stating that methods of treating cancer are provided, comprising administering an engineered immune cell comprising an exogenous nucleic acid molecule and at least one of:
One or more endogenous genes encoding a NKG2D ligand that have been engineered to be inactivated;
One or more inhibitors directed against one or more NKG2D ligands.
to a subject in need thereof.

The methods for treatment can be autologous methods (the subject receives cells that originated from his or her body) or can be allogeneic methods (the immune cells are derived from a donor that is not the subject).

According to specific embodiments, the inhibition of NKG2D ligands (i.e. the engineering to inactivate the genes, or the addition of one or more inhibitors) continues while the drug is administered to the patient (e.g. because the ligand is knocked out, or e.g. because shRNA is introduced that is constitutively expressed).

DETAILED DESCRIPTION

Definitions

Figure 1:
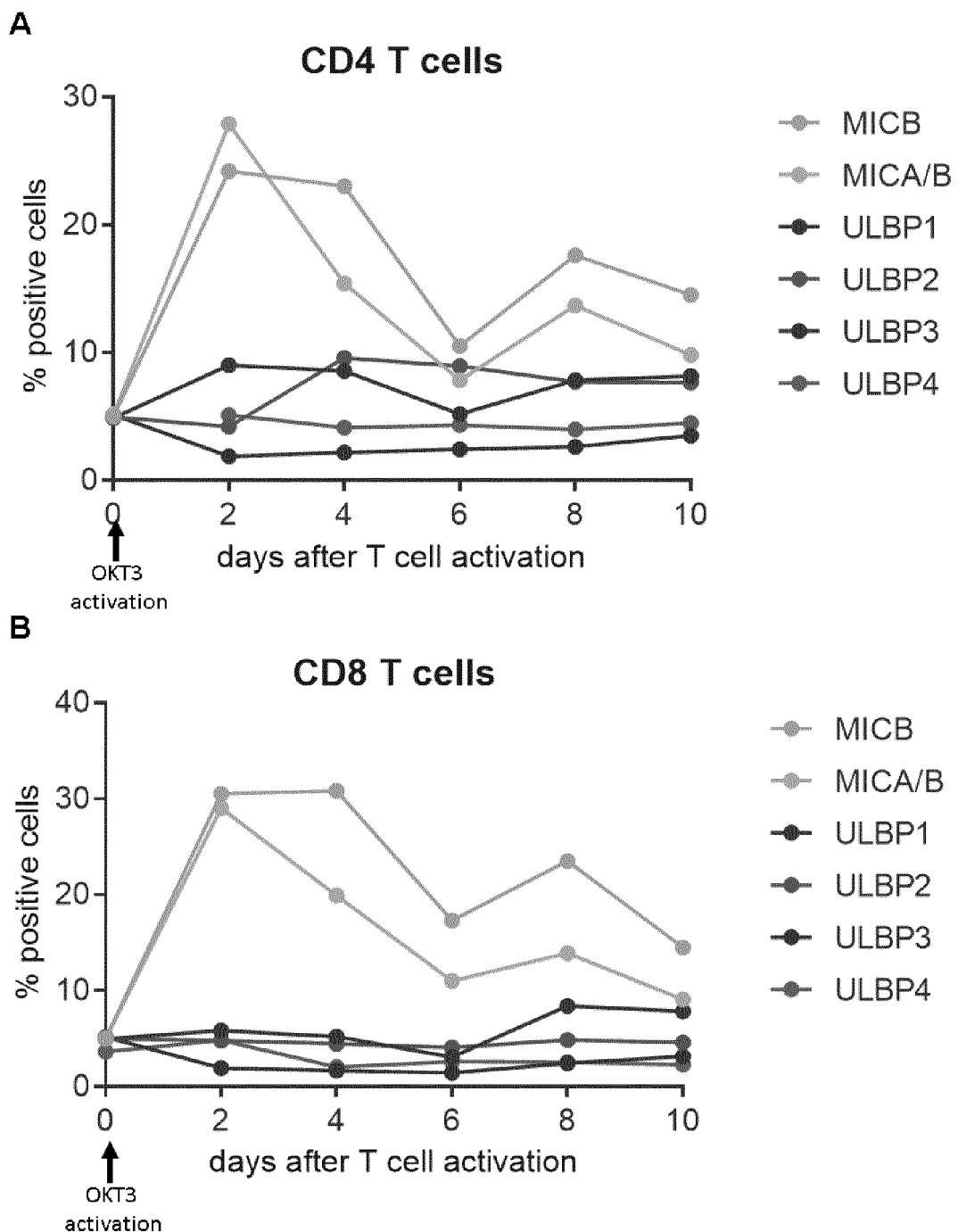
FIG. 1. Expression of NKG2D ligands on the surface of CD4+(A) and CD8+(B) T cells FIG. 2. Screening of shRNAs targeting both MICA and MICB. % protein expression of MICA/B or MICB remaining upon cotransfection with selected shRNAs FIG. 3. Design of a single CAR+shRNA vector FIG. 4. Co-expression of MICA/B targeting shRNA reduces fratricide FIG. 5. Reducing fratricide increases killing of cancer cells FIG. 6. MICA/B targeting shRNAs improve in vivo engraftment of NKG2D CAR-T cells FIG. 7. Tumor burden at individual days in a mouse AML model treated with NKR2 with and without shRNA against MICA/B. BLI=bioluminescence intensity FIG. 8. Survival curve of a mouse AML model treated with mock cells or NKR2 with and without shRNA against MICA/B.

The present invention will be described with respect to particular embodiments and with reference to certain drawings but the invention is not limited thereto but only by the claims. Any reference signs in the claims shall not be construed as limiting the scope. The drawings described are only schematic and are non-limiting. In the drawings, the size of some of the elements may be exaggerated and not drawn on scale for illustrative purposes. Where the term "comprising" is used in the present description and claims, it does not exclude other elements or steps. Where an indefinite or definite article is used when referring to a singular noun e.g. "a" or "an", "the", this includes a plural of that noun unless something else is specifically stated.

Furthermore, the terms first, second, third and the like in the description and in the claims, are used for distinguishing between similar elements and not necessarily for describing a sequential or chronological order. It is to be understood that the terms so used are interchangeable under appropriate circumstances and that the embodiments of the invention described herein are capable of operation in other sequences than described or illustrated herein.

The following terms or definitions are provided solely to aid in the understanding of the invention.

Unless specifically defined herein, all terms used herein have the same meaning as they would to one skilled in the art of the present invention. Practitioners are particularly directed to Green and Sambrook, Molecular Cloning: A Laboratory Manual, 4th ed., Cold Spring Harbor Laboratory Press, New York (2012); and Ausubel et al., Current Protocols in Molecular Biology (up to Supplement 114), John Wiley & Sons, New York (2016), for definitions and terms of the art. The definitions provided herein should not be construed to have a scope less than understood by a person of ordinary skill in the art.

The term "immune cells" as used herein refers to cells that are part of the immune system (which can be either the adaptive or the innate immune system). Particularly envisaged immune cells include white blood cells (leukocytes), including lymphocytes, monocytes, macrophages and dendritic cells. Particularly envisaged lymphocytes include T cells, NK cells and B cells, most particularly envisaged are T cells. Immune cells as used herein are typically immune cells that are manufactured for adoptive cell transfer (either autologous transfer or allogeneic transfer). In the context of adoptive transfer, note that immune cells will typically be primary cells (i.e. cells isolated directly from human or animal tissue, and not or only briefly cultured), and not cell lines (i.e. cells that have been continually passaged over a long period of time and have acquired homogenous genotypic and phenotypic characteristics). According to specific embodiments, the immune cell is a primary cell. According to alternative specific embodiments, the immune cell is not a cell from a cell line.

The term "exogenous" as used herein in the context of immune cells refers to any material that is present and active in an individual living cell but that originated outside that cell (as opposed to an endogenous factor). The phrase "exogenous nucleic acid molecule" thus refers to a nucleic acid molecule that has been introduced in the immune cell, typically through transduction or transfection. The term "endogenous" as used herein refers to any factor or material that is present and active in an individual living cell and that originated from inside that cell (and that are thus typically also manufactured in a non-transduced or non-transfected cell).

The term "NKG2D ligand" or the plural "NKG2D ligands" as used in the application refers to the human genes MICA (Gene ID: 100507436), MICB (Gene ID: 4277), ULBP1 (Gene ID: 80329), ULBP2 (Gene ID: 80328), ULBP3 (Gene ID: 79465), ULBP4 or RAET1E (Gene ID: 135250), ULBP5 or RAET1G (Gene ID: 353091), ULBP6 or RAETIL (Gene ID: 154064) and their gene products (or the relevant homolog when cells of other species are used). Encompassed within the term gene products is at least RNA (transcribed from the gene) and protein (encoded by the NKG2D ligand gene, and translated from the transcribed RNA).

An "inhibitor directed against a NKG2D ligand" or "a NKG2D ligand inhibitor" as used herein refers to a molecule that prevents, inhibits or reduces signaling through the NKG2D ligand. Inhibition can occur at the DNA, RNA or protein level, e.g. through prevention of transcription or translation, through contact inhibition, competitive inhibition or other means.

The term "inhibition of one or more NKG2D ligands" as used in the application refers to interference with the function of the gene product of one or more of the NKG2D ligands, either at the DNA level (by inhibiting the formation of NKG2D ligand gene product, i.e. by preventing or interfering with transcription), at the RNA level (by neutralizing or destabilizing mRNA to prevent or interfere with translation) or at the protein level (by neutralizing or inhibiting the one or more NKG2D ligands, or by targeting nascent protein during the translation process). Neutralizing at the protein level can be achieved at the cellular surface (e.g. by inhibiting receptor-ligand interaction) or before the protein is expressed at the surface (e.g. by retaining the protein in an intracellular organelle). Typically, the ultimate functional effect of inhibition of one or more NKG2D ligands will be inhibition of NK cell cell activation through NKG2D-mediated signals.

Inhibition of one or more NKG2D ligands does not necessarily mean complete ablation of the NKG2D-induced signal, although this is envisaged as well. Particularly with antisense RNA and siRNA, but with antibodies as well, it is known that inhibition is often partial inhibition rather than complete inhibition. However, lowering functional NKG2D ligand levels may have a beneficial effect even when complete inhibition is not achieved as it lowers the chance of the immune cells being cleared.

Thus, according to particular embodiments, the inhibition will result in a decrease of 10%, 20%, 25%, 30%, 40%, 50%, 60%, 70%, 75%, 80%, 90% or up to 100% of the gene product of one or more of NKG2D ligands. Methods of measuring the levels of NKG2D ligand gene product are known to the skilled person, and these can be measured before and after the addition of the inhibitor to assess the decrease in levels of functional gene product, or can be compared to suitable control cells where the ligands are not inhibited. Similarly, the inhibition may result in a decrease of 10%, 20%, 25%, 30%, 40%, 50%, 60%, 70%, 75%, 80%, 90% or up to 100% of NK cell-mediated lysis as compared to cells in which no NKG2D ligand is inhibited.

A "chimeric antigen receptor" or "CAR" as used herein refers to a chimeric receptor (i.e. composed of parts from different sources) that has at least a binding moiety with a specificity for an antigen (which can e.g. be derived from an antibody or a receptor) and a signaling moiety that can transmit a signal in an immune cell (e.g. a CD3 zeta chain). A "TCR" as used herein refers to a T cell receptor. In the context of adoptive cell transfer, this typically refers to an engineered TCR, i.e. a TCR that has been engineered to recognize a specific antigen, most typically a tumor antigen.

The term "clearance" as used herein refers to the removal of cells from the circulation, tissue or body —most typically, it refers to the removal of the introduced immune cells, e.g. from the circulation. "Clearance by NK cells" in this context means that the clearance is mediated by natural killer cells, NK cells typically clear or kill other cells by inducing lysis or apoptosis of these cells.

The present application is the first to show that immune cells in which NKG2D ligands have been inactivated or inhibited are less sensitive to clearance by NK cells and thus are more effective as a therapeutic as they remain active for longer. This is based on the finding that it appears the transduction and culture of immune cells (patient cells or donor cells) to make them suitable for adoptive cell transfer (i.e., the manufacturing process of ACT cells) also increases the presence of induced self antigens, including NKG2D ligands, and that this is effectively a cause of clearance from circulation by NK cells.

Accordingly, it is an object of the invention to provide engineered immune cells containing at least one or more endogenous genes encoding a NKG2D ligand engineered to be inactivated; and/or one or more inhibitors directed against one or more endogenous NKG2D ligands.

Of note, although NKG2D is the best studied receptor involved in recognition of induced-self antigens, it is not the only NK receptor in this family that recognizes stress-induced ligands (or induced self antigens, or markers of the abnormal self, all used as equivalents herein). Other natural killer cell receptors that are able to bind induced-self antigens are NKG2C, NKG2E, NKG2F, NKG2H (like NKG2D, all CD94 molecules) or Natural Cytotoxicity Receptors (NCR) such as NKp 46, NKp30 and NKp44, and it is envisaged that the methods and compositions can be used for such chimeric receptors as well, *mutatis mutandis*. Thus, wherever NKG2D is used in the application, this also applies to NKG2C, NKG2E, NKG2F, NKG2H, NKp46, NKp30 and NKp44. Note that the ligands for NKG2C, E, F and H are nonclassical MHC glycoproteins class I (HLA-E in human).

As these engineered cells are less sensitive to clearance, it is also an object of the invention to provide methods of rendering an immune cell less sensitive to clearance by NK cells, comprising the step of inhibition of one or more NKG2D ligands in the immune cell. This inhibition can be achieved through genetic inactivation, or by the presence of a NKG2D ligand inhibitor in the cell. Of note, while the clearance of NK cells is a process that happens in the body, the methods provided herein are in vitro or ex vivo methods. Indeed, the inhibition step (either through genetic engineering/inactivation or by the introduction of an inhibitory molecule) happens during the manufacturing process of said cells to make them suitable for ACT, and will be done outside a human body, i.e. not in the patient (that will receive the ACT cells) or in the donor (that is the source of the immune cells, and which can be the same or a different person, depending on whether the therapy is autologous or allogeneic). In other words, the methods described herein are applicable during manufacturing of immune cells.

Typically, manufacturing of immune cells occurs when cells are being prepared or cultured for adoptive transfer. This can be autologous adoptive transfer (a subject receives his own cells that have been modified and/or expanded), or allogeneic adoptive transfer (a subject receives cells from a different individual). Thus, according to specific embodiments, in vitro methods are provided for rendering an immune cell less sensitive to clearance by NK cells, and these methods do not encompass the administration to the patient.

The cells typically will further comprise an exogenous nucleic acid molecule. According to specific embodiments, the nucleic acid molecule encodes a chimeric antigen receptor (CAR) or a TCR. This CAR or TCR can be directed against a suitable target. Most typically, the CAR or TCR will be directed against a tumor target. By way of non-limiting examples, the CAR or TCR can be directed e.g. against B7H6, BCMA, CAIX, CD7, CD16, CD19, CD20, CD22, CD27 (TNFRSF7), CD30 (TNFRSF8), CD33, CD38, CD52, CD56, CD70 (TNFSF7), CD123 (IL3R alpha), CD133, CEA, CLD18 (claudin 18, splice variant 2), CLL1, cMET, CS1, EGFR, EGFRvIII, EpCAM, ErbB123, FAP (fibroblast activation protein), folate receptor alpha, GD2, GPC3, HER1, HER2 (also Neu, ErbB2 or CD340), IL-1A, IL13R alpha 2 (CD213A2), kappa light chain, L1-CAM, LeY, mesothelin, MUC-1, MUC16, NKG2D, NKp30, NKp44, NKp46, NY-ESO1, PD-1, PDL-1, PlGF, PSCA, PSMA, ROR-1, or VEGFR2.

Inhibition can occur in multiple ways: contact inhibition (competitive inhibition or non-competitive inhibition), inhibition by interfering with ligand or receptor expression, interfering with ligand or receptor localization (e.g. preventing migration to cell surface), inhibition by binding to ligand or receptor or preventing interaction of both, and inhibition of downstream signaling, to name a few.

Permanent inhibition of the one or more of the NKG2D ligands is typically achieved by genetic knockdown. It has indeed been shown that gene editing is one potential method to specifically eliminate target antigen expression in the engineered T cell (Gomes-Silva D et al., Blood, 2017). However, given the potential expression of eight different ligands, gene editing technology to eliminate all these polymorphic targets presents a challenge, so it is particularly envisaged when only one or a few ligands need to be permanently inactivated. Genetic inhibition (i.e. engineering to inactivate a gene) can be replaced or complemented with other approaches.

In general, functional inhibition can be achieved at three levels. First, at the DNA level, e.g. by removing or disrupting a gene (here a NKG2D ligand gene) in said immune cells, or preventing transcription to take place (in both instances preventing synthesis of the gene product). Second, at the RNA level, e.g. by preventing efficient translation to take place—this can be through destabilization of the mRNA so that it is degraded before translation occurs from the transcript, or by hybridizing to the mRNA. Third, at the protein level, e.g. by binding to the protein, inhibiting its function, retaining the protein at a different cellular location and/or marking the protein for degradation.

If inhibition is to be achieved at the DNA level, this may be done using gene therapy to knock-out or disrupt the gene. As this typically results in permanent inhibition, this is particularly envisaged for inhibition of NKG2D ligands in the immune cells. As used herein, a "knock-out" can be a gene knockdown or the gene can be knocked out by a mutation such as, a point mutation, an insertion, a deletion, a frameshift, or a missense mutation by techniques known in the art, including, but not limited to, retroviral gene transfer. Another way in which genes can be knocked out is by the use of engineered nucleases. Examples of such engineered nucleases include, but are not limited to, meganucleases, zinc finger nucleases, TALENs, megaTALs and CRISPR nucleases.

Meganucleases, found commonly in microbial species, have the unique property of having very long recognition sequences (>14 bp) for making site-specific double strand breaks in nucleic acids. This makes them naturally very specific for a target sequence, and through mutagenesis and high throughput screening, hybrid meganuclease variants can be made that recognize unique sequences. As opposed to meganucleases, the concept behind ZFNs and TALEN technology is based on a non-specific DNA cutting enzyme, which can then be linked to specific DNA sequence recognizing peptides such as zinc fingers and transcription activator-like effectors (TALEs). Zinc-finger nucleases (ZFNs) are artificial restriction enzymes generated by fusing a zinc finger DNA-binding domain to a DNA-cleavage domain. Zinc finger domains can be engineered to target desired DNA sequences, which enable zinc-finger nucleases to target unique sequence within a complex genome. By taking advantage of endogenous DNA repair machinery, these reagents can be used to precisely alter the genomes of higher organisms. TALENs work similar to zinc fingers, but rely on transcription activator-like effectors (TALEs) for DNA recognition. TALEs are found in repeats with a one-to-one recognition ratio between the amino acids and the recognized nucleotide pairs. Because TALEs happen in repeated patterns, different combinations can be tried to create a wide variety of sequence specificities.

MegaTALs are derived from the combination of two distinct classes of DNA targeting enzymes. Meganucleases (also referred to as homing endonucleases) are single peptide chains that have the advantage of both DNA recognition and nuclease functions in the same domain. However, meganuclease target recognition is difficult to modify, and they often have reduced specificity and lower on-target cleavage efficiency than other genome targeting endonucleases. Transcription activator-like (TAL) effectors are DNA recognizing proteins that have been linked to separate DNA endonuclease domains in order to achieve a targeted DNA double strand break. In contrast to meganucleases, TALs are easily engineered to target specific DNA sequences. Current platforms rely on a pair of TAL effectors, each coupled to a non-specific DNA cleavage domain, in which DNA cleavage only occurs when both TAL effectors bind their respective sequences and the two endonuclease domains dimerize in order to cleave the DNA. However, TAL effector nucleases can cause off-target activity, are much larger than meganucleases, and require the delivery of two separate proteins. A megaTAL is the unification of a TAL effector with a meganuclease.

CRISPR/Cas (Clustered Regularly Interspaced Short Palindromic Repeats/Crispr associated protein) is a genome editing technology using a modified version of a prokaryotic defence mechanism, and allows permanent modification of genes within organisms. By delivering the Cas (typically Cas9) nuclease complexed with a synthetic guide RNA (gRNA) into a cell, the cell's genome can be cut at a desired location, allowing existing genes to be removed and/or new ones added.

Genetic knockdown of one or more NKG2D ligand genes in the immune cells may mean inhibition of any combination of MICA, MICB, ULBP1, ULBP2, ULBP3, ULBP4, ULBP5 and ULBP6; and thus may mean knockout of one, two, three, four, five, six, seven or eight genes.

Apart from genetic inactivation of NKG2D ligands, inhibition of one or more NKG2D ligands can also be achieved by (typically transient) inhibition using an inhibitor. Inhibitors may act by inhibition of one or more NKG2D ligands on the immune cells, but also by inhibition of proper localization of the NKG2D ligands.

The timeframe of inhibition/introducing the inhibitor will typically coincide with the timeframe of manufacturing of the immune cells for ACT. These manufacturing protocols may vary in number and order of steps, but they typically contain a transduction step (in which e.g. a CAR is introduced in the isolated immune cells), an expansion step (in which the cells are cultured and increase in number) and a harvesting step (in which the cells are isolated and reformulated or concentrated, prior to administration to a patient or for (cryo)preservation). The step of introducing the inhibitor (or doing the engineering for gene inactivation) will particularly coincide with the transduction step.

One form of inhibition is by transient gene inactivation. Transient gene inactivation may for instance be achieved through expression of antisense RNA in the immune cells, or by administering antisense RNA to said cells. An antisense construct can be delivered, for example, as an expression plasmid, which, when transcribed in the cell, produces RNA that is complementary to at least a unique portion of the target mRNA (here mRNA of a NKG2D ligand).

A more rapid method for the inhibition of gene expression is based on the use of shorter antisense oligomers consisting of DNA, or other synthetic structural types such as phosphorothiates, 2'-O-alkylribonucleotide chimeras, locked nucleic acid (LNA), peptide nucleic acid (PNA), or morpholinos. With the exception of RNA oligomers, PNAs and morpholinos, all other antisense oligomers act in eukaryotic cells through the mechanism of RNase H-mediated target cleavage. PNAs and morpholinos bind complementary DNA and RNA targets with high affinity and specificity, and thus act through a simple steric blockade of the RNA translational machinery, and appear to be completely resistant to nuclease attack. An "antisense oligomer" refers to an anti-sense molecule or anti-gene agent that comprises an oligomer of at least about 10 nucleotides in length. In embodiments an antisense oligomer comprises at least 15, 18 20, 25, 30, 35, 40, or 50 nucleotides. Antisense approaches involve the design of oligonucleotides (either DNA or RNA, or derivatives thereof) that are complementary to an mRNA encoded by polynucleotide sequences of FMR1. Antisense RNA may be introduced into a cell to inhibit translation of a complementary mRNA by base pairing to it and physically obstructing the translation machinery. This effect is therefore stoichiometric. Absolute complementarity, although preferred, is not required. A sequence "complementary" to a portion of an RNA, as referred to herein, means a sequence having sufficient complementarity to be able to hybridize with the RNA, forming a stable duplex; in the case of double-stranded antisense polynucleotide sequences, a single strand of the duplex DNA may thus be tested, or triplex formation may be assayed. The ability to hybridize will depend on both the degree of complementarity and the length of the antisense polynucleotide sequence. Generally, the longer the hybridizing polynucleotide sequence, the more base mismatches with an RNA it may contain and still form a stable duplex (or triplex, as the case may be). One skilled in the art can ascertain a tolerable degree of mismatch by use of standard procedures to determine the melting point of the hybridized complex. Oligomers that are complementary to the 5' end of the message, e.g., the 5' untranslated region (UTR) up to and including the AUG translation initiation codon, should work most efficiently at inhibiting translation. However, sequences complementary to the 3' UTR of mRNAs have recently been shown to be effective at inhibiting translation of mRNAs as well (Wagner, R. (1994) Nature 372, 333-335). Therefore, oligomers complementary to either the 5', 3' UTRs, or non-coding regions of the target gene could be used in an antisense approach to inhibit translation of said endogenous mRNA encoded by the target gene. Oligomers complementary to the 5' UTR of said mRNA should include the complement of the AUG start codon. Antisense oligomers complementary to mRNA coding regions are less efficient inhibitors of translation but could be used in accordance with the invention. Whether designed to hybridize to the 5', 3' or non-coding region of a said mRNA, antisense oligomers should be at least 10 nucleotides in length, and are preferably oligomers ranging from 15 to about 50 nucleotides in length. In certain embodiments, the oligomer is at least 15 nucleotides, at least 18 nucleotides, at least 20 nucleotides, at least 25 nucleotides, at least 30 nucleotides, at least 35 nucleotides, at least 40 nucleotides, or at least 50 nucleotides in length. A related method uses ribozymes instead of antisense RNA. Ribozymes are catalytic RNA molecules with enzyme-like cleavage properties that can be designed to target specific RNA sequences. Successful target gene inactivation, including temporally and tissue-specific gene inactivation, using ribozymes has been reported in mouse, zebrafish and fruit flies. RNA interference (RNAi) is a form of post-transcriptional gene silencing. The phenomenon of RNA interference was first observed and described in *Caenorhabditis elegans* where exogenous double-stranded RNA (dsRNA) was shown to specifically and potently disrupt the activity of genes containing homologous sequences through a mechanism that induces rapid degradation of the target RNA. Several reports describe the same catalytic phenomenon in other organisms, including experiments demonstrating spatial and/or temporal control of gene inactivation, including plant (*Arabidopsis thaliana*), protozoan (*Trypanosoma bruceii*), invertebrate (*Drosophila melanogaster*), and vertebrate species (*Danio rerio* and *Xenopus laevis*). The mediators of sequence-specific messenger RNA degradation are small interfering RNAs (siRNAs) generated by ribonuclease Ill cleavage from longer dsRNAs. Generally, the length of siRNAs is between 20-25 nucleotides (Elbashir et al. (2001) Nature 411, 494-498). The siRNA typically comprise a sense RNA strand and a complementary antisense RNA strand annealed together by standard Watson Crick base pairing interactions (hereinafter "base paired"). The sense strand comprises a nucleic acid sequence that is identical to a target sequence contained within the target mRNA. The sense and antisense strands of the present siRNA can comprise two complementary, single stranded RNA molecules or can comprise a single molecule in which two complementary portions are base paired and are covalently linked by a single stranded "hairpin" area (often referred to as shRNA). These artificial RNA molecules with a tight hairpin turn are particularly envisaged for gene silencing and are included in the term siRNA. The term "isolated" means altered or removed from the natural state through human intervention. For example, an siRNA naturally present in a living animal is not "isolated," but a synthetic siRNA, or an siRNA partially or completely separated from the coexisting materials of its natural state is "isolated." An isolated siRNA can exist in substantially purified form, or can exist in a non-native environment such as, for example, a cell into which the siRNA has been delivered.

The siRNAs of the invention can comprise partially purified RNA, substantially pure RNA, synthetic RNA, or recombinantly produced RNA, as well as altered RNA that differs from naturally occurring RNA by the addition, deletion, substitution and/or alteration of one or more nucleotides. Such alterations can include addition of non-nucleotide material, such as to the end(s) of the siRNA or to one or more internal nucleotides of the siRNA, including modifications that make the siRNA resistant to nuclease digestion.

One or both strands of the siRNA of the invention can also comprise a 3' overhang. A "3' overhang" refers to at least one unpaired nucleotide extending from the 3' end of an RNA strand. Thus, in one embodiment, the siRNA of the invention comprises at least one 3' overhang of from one to about six nucleotides (which includes ribonucleotides or deoxynucleotides) in length, preferably from one to about five nucleotides in length, more preferably from one to about four nucleotides in length, and particularly preferably from about one to about four nucleotides in length.

In the embodiment in which both strands of the siRNA molecule comprise a 3' overhang, the length of the overhangs can be the same or different for each strand. In a most preferred embodiment, the 3' overhang is present on both strands of the siRNA, and is two nucleotides in length. In order to enhance the stability of the present siRNAs, the 3' overhangs can also be stabilized against degradation. In one embodiment, the overhangs are stabilized by including purine nucleotides, such as adenosine or guanosine nucleotides.

Alternatively, substitution of pyrimidine nucleotides by modified analogues, e.g., substitution of uridine nucleotides in the 3' overhangs with 2' deoxythymidine, is tolerated and does not affect the efficiency of RNAi degradation. In particular, the absence of a 2' hydroxyl in the 2' deoxythymidine significantly enhances the nuclease resistance of the 3' overhang in tissue culture medium. siRNAs can be obtained using a number of techniques known to those of skill in the art. For example, the siRNAs can be chemically synthesized or recombinantly produced using methods known in the art. Preferably, the siRNA of the invention are chemically synthesized using appropriately protected ribonucleoside phosphoramidites and a conventional DNA/RNA synthesizer. The siRNA can be synthesized as two separate, complementary RNA molecules, or as a single RNA molecule with two complementary regions. Commercial suppliers of synthetic RNA molecules or synthesis reagents include Proligo (Hamburg, Germany), Dharmacon Research (Lafayette, Colo., USA), Pierce Chemical (part of Perbio Science, Rockford, Ill., USA), Glen Research (Sterling, Va., USA), ChemGenes (Ashland, Mass., USA) and Cruachem (Glasgow, UK).

Alternatively, siRNA can also be expressed from recombinant circular or linear DNA plasmids using any suitable promoter. Suitable promoters for expressing siRNA of the invention from a plasmid include, for example, the U6 or H1 RNA pol IIiI promoter sequences and the cytomegalovirus promoter. Selection of other suitable promoters is within the skill in the art. The recombinant plasmids of the invention can also comprise inducible or regulatable promoters for expression of the siRNA in a particular tissue or in a particular intracellular environment. The siRNA expressed from recombinant plasmids can either be isolated from cultured cell expression systems by standard techniques, or can be expressed intracellularly, e.g. in breast tissue or in neurons.

The siRNAs of the invention can also be expressed intracellularly from recombinant viral vectors. The recombinant viral vectors comprise sequences encoding the siRNAs of the invention and any suitable promoter for expressing the siRNA sequences. Suitable promoters include, for example, the U6 or H1 RNA pol III promoter sequences and the cytomegalovirus promoter. Selection of other suitable promoters is within the skill in the art. The recombinant viral vectors of the invention can also comprise inducible or regulatable promoters for expression of the siRNA in the tissue where the tumour is localized.

As used herein, an "effective amount" of the siRNA is an amount sufficient to cause RNAi mediated degradation of the target mRNA, or an amount sufficient to reduce NKG2D ligand-induced signaling in NK cells. RNAi mediated degradation of the target mRNA can be detected by measuring levels of the target mRNA or protein in the cells of a subject, using standard techniques for isolating and quantifying mRNA or protein as described above.

It has been shown that morpholino antisense oligonucleotides in zebrafish and frogs overcome the limitations of RNase H-competent antisense oligonucleotides, which include numerous non-specific effects due to the non target-specific cleavage of other mRNA molecules caused by the low stringency requirements of RNase H. Morpholino oligomers therefore represent an important new class of antisense molecule. Oligomers of the invention may be synthesized by standard methods known in the art. As examples, phosphorothioate oligomers may be synthesized by the method of Stein et al. (1988) Nucleic Acids Res. 16, 3209-3021), methylphosphonate oligomers can be prepared by use of controlled pore glass polymer supports (Sarin et al. (1988) Proc. Natl. Acad. Sci. USA. 85, 7448-7451). Morpholino oligomers may be synthesized by the method of Summerton and Weller U.S. Pat. Nos. 5,217,866 and 5,185,444.

Inhibition, particularly transient inhibition, can also be achieved by inhibitors at the protein level. A typical example thereof are antibodies against one or more of the NKG2D ligands.

The term 'antibody' or 'antibodies' relates to an antibody characterized as being specifically directed against the NKG2D ligand or any functional derivative thereof, with said antibodies being preferably monoclonal antibodies; or an antigen-binding fragment thereof, of the F(ab')2, F(ab) or single chain Fv type, or any type of recombinant antibody derived thereof. These antibodies of the invention, including specific polyclonal antisera prepared against the target protein or any functional derivative thereof, have no cross-reactivity to other proteins. The monoclonal antibodies of the invention can for instance be produced by any hybridoma liable to be formed according to classical methods from splenic cells of an animal, particularly of a mouse or rat immunized against the target protein or any functional derivative thereof, and of cells of a myeloma cell line, and to be selected by the ability of the hybridoma to produce the monoclonal antibodies recognizing the target protein or any functional derivative thereof which have been initially used for the immunization of the animals. The monoclonal antibodies according to this embodiment of the invention may be humanized versions of the mouse monoclonal antibodies made by means of recombinant DNA technology, departing from the mouse and/or human genomic DNA sequences coding for H and L chains or from cDNA clones coding for H and L chains. Alternatively the monoclonal antibodies according to this embodiment of the invention may be human monoclonal antibodies. Such human monoclonal antibodies are prepared, for instance, by means of human peripheral blood lymphocytes (PBL) repopulation of severe combined immune deficiency (SCID) mice as described in PCT/EP 99/03605 or by using transgenic non-human animals capable of producing human antibodies as described in U.S. Pat. No. 5,545,806. Also fragments derived from these monoclonal antibodies such as Fab, F(ab)'2 and scFv ("single chain variable fragment"), providing they have retained the original binding properties, form part of the present invention. Such fragments are commonly generated by, for instance, enzymatic digestion of the antibodies with papain, pepsin, or other proteases. It is well known to the person skilled in the art that monoclonal antibodies, or fragments thereof, can be modified for various uses. The antibodies involved in the invention can be labeled by an appropriate label of the enzymatic, fluorescent, or radioactive type. In a particular embodiment said antibodies against a target protein or a functional fragment thereof are derived from camels. Camel antibodies are fully described in WO94/25591, WO94/04678 and in WO97/49805.

Other inhibitors of NKG2D ligands at the protein level include, but are not limited to, peptide inhibitors of NKG2D ligands, peptide-aptamer (Tomai et al., J Biol Chem. 2006) inhibitors of NKG2D ligands, and protein interferors or Pept-Ins™ as described in WO2007/071789 or WO2012/123419, incorporated herein by reference.

Another way of inhibition at the protein level is by interfering with the secretory transport, so that the ligands are not transported to the cell membrane. Typically, this is a temporary form of inhibition and normal cellular location can be restored when the appropriate signal is given to the cells, however, if no such signal is given, the inhibition will be permanent. An exemplary method according to this principle is the RUSH (retention using selective hooks) system (Boncompain et al., Nature Methods 2012 and WO2010142785).

Small molecule inhibitors, e.g. small organic molecules, and other drug candidates can be obtained, for example, from combinatorial and natural product libraries.

Thus, NKG2D ligand inhibitors are typically selected from siRNA, antibodies, peptide inhibitors; more particularly they are selected from siRNA or antibodies; most particularly they are siRNA (such as e.g. shRNA) molecules against one or more NKG2D ligands.

Many different types of immune cells are used for adoptive therapy and thus are envisaged for use in the methods described herein. Examples of immune cells include, but are not limited to, T cells, NK cells, NKT cells, lymphocytes, dendritic cells, myeloid cells, stem cells or iPSCs. The latter two are not immune cells as such, but can be used in adoptive cell transfer for immunotherapy (see e.g. Jiang et al., Cell Mol Immunol 2014; Themeli et al., Cell Stem Cell 2015). Typically, while the manufacturing starts with stem cells or iPSCs (or may even start with a dedifferentiation step from immune cells towards iPSCs), manufacturing will entail a step of differentiation to immune cells prior to administration. As the instant methods relate to the manufacturing process (i.e., the steps prior to administration), stem cells and iPSCs used in manufacturing of immune cells for adoptive transfer are considered as immune cells herein. According to particular embodiments, the stem cells envisaged in the methods do not involve a step of destruction of a human embryo.

Particularly envisaged cells for use in the instant methods are T cells and NK cells. According to a further aspect, the engineered immune cells described herein are provided for use as a medicament. According to still a further aspect, the engineered immune cells described herein are provided for use in the treatment of diseases selected from inflammatory disease, cancer, or infection (e.g. viral, bacterial, fungal infection). As cell therapy is quite expensive, it is particularly envisaged for life-threatening diseases. Accordingly, most particularly, the cells and compositions described herein are provided for use in the treatment of cancer. Whereas in principle all cancers can be treated, including, but not limited to, bladder cancer, brain cancer, breast cancer, cervical cancer, colorectal cancer, esophageal cancer, glioblastoma, head and neck cancer, kidney cancer, leukemia, liver cancer, lung cancer, lymphoma, melanoma, mesothelioma, multiple myeloma, ovarian cancer, pancreatic cancer, prostate cancer, sarcoma, stomach cancer and thyroid cancer; most particularly envisaged cancers include leukemia (including AML), multiple myeloma, bladder cancer, breast cancer, colorectal cancer, ovarian cancer, and pancreatic cancer.

That the immune cells are provided for use in treatment is equivalent as saying that methods of treating disease are provided, comprising a step of administering these immune cells to a subject in need thereof. Thus, according to these embodiments, methods of treating inflammatory disease are provided comprising administering the cells to a subject in need thereof. Likewise, methods of treating cancer are provided comprising administering the cells to a subject in need thereof. Similarly, methods of treating infection are provided comprising administering the cells to a subject in need thereof.

Particularly envisaged are methods of treating cancer in a subject in need thereof, comprising a step of administering an engineered immune cell to said subject, the immune cell containing an exogenous nucleic acid molecule and at least one of:
One or more endogenous genes encoding a NKG2D ligand that have been engineered to be inactivated;
One or more inhibitors directed against one or more NKG2D ligands.

Most particularly, the exogenous nucleic acid molecule encodes a chimeric antigen receptor or a TCR. Typical targets for such CARs or TCRs are listed above.

The immune cells may be autologous to the subject to which the cells are to be administered, or may be allogeneic, i.e. originating from a different subject.

It is to be understood that although particular embodiments, specific configurations as well as materials and/or molecules, have been discussed herein for cells and methods according to present invention, various changes or modifications in form and detail may be made without departing from the scope and spirit of this invention. The following examples are provided to better illustrate particular embodiments, and they should not be considered limiting the application. The application is limited only by the claims.

EXAMPLES

Example 1. T Cell Activation Induces Specific NKG2D Ligand Expression

This example demonstrates the generation of an engineered immune cell, more particularly a T cell, comprising a chimeric NKG2D receptor (i.e. an exogenous nucleic acid molecule encoding a chimeric antigen receptor) and one or more shRNAs directed against one or more NKG2D ligands. These shRNAs are obtained from Dharmacon (SMARTvector).

As a first step, it was assessed which ligands for NI(cell receptors are most commonly expressed on T cells, particularly on activated T cells, as these are the ligands that make these cells a target for NK-mediated killing. Particular focus was on NKG2D ligands, as these are known to be specifically induced. Indeed, NKG2D is known to engage 8 different stress-induced ligands (NKG2DL) broadly present on tumors but largely absent on healthy tissues. We aimed to identify the key NKG2DL expressed on T cells upon activation. PBMCs were activated at day 0 with OKT3 and anti-CD3 antibody. The expression of the eight NKG2DL was assessed every other day on the surface of CD4+ and CD8+ T cells (FIG. 1). Upon activation, MICA/B and MICB were upregulated on the cell surface of CD4 and CD8 T cells, with expression peaking at day 2-4 after activation. Subsequently, expression declined until day 10. ULBP1 and ULBP2 were expressed at low levels, whereas ULBP2 was restricted to CD4+ T cells (FIG. 1). There was little evidence of expression of the other ligands on T cells.

Figure 2:
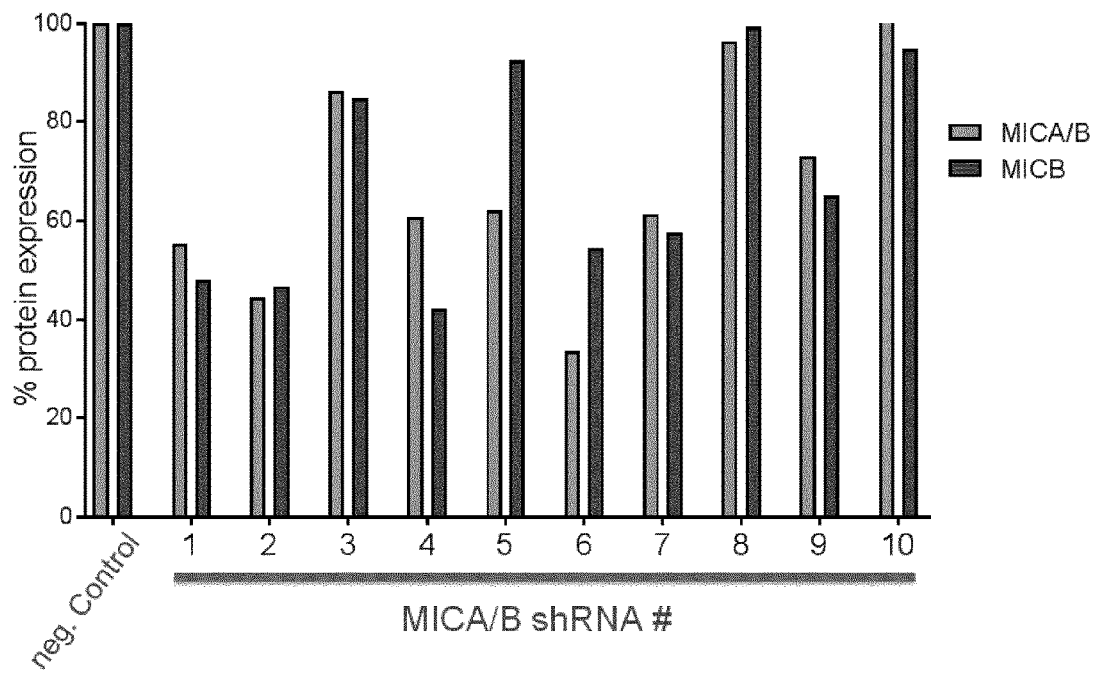

We then explored specific targeting of both MICA and MICB with a single shRNA, feasible since there is a high sequence similarity. Primary T cells were transduced with the different shRNAs and MICA and MICB protein expression was assessed. This screen identified two shRNAs to reduce cell surface expression of MICA and MICB (FIG. 2 and Table 1).

reduced in vitro fratricide (FIG. 4), compared to cells without the shRNA and enhanced the rate of expansion of NKG2D CAR T cells approaching that of control T cells. Thus, inhibiting NKG2D ligands makes the cells less sensitive to killing by NK receptors.

Subsequently, we assessed the in vitro anti-tumor efficacy of NKG2D based CAR T cells with and without MICA/B-targeting shRNAs. Cells lacking the shRNA showed specific killing of AML HL-60 cells at the different effector to target (E:T) ratios. However, co-expression of MICA/B shRNA #2

TABLE 1

Target sequence and sense and antisense design of the shRNAs of FIG. 2.

| Target | Sense Design | Antisense Design |
|---|---|---|
| CAGGATGGGGTATCTTTGA (SEQ ID NO: 1) | GGCTTCAAAGATACCCCATCCTGGGGATTGAGTTTTGAACTCCAGGATGCGGTATCTTTG (SEQ ID NO: 11) | ACTCCAAAGATACCGCATCCTGGAGTTCAAAACTCAATCCCCAGGATGGGGTATCTTTGA (SEQ ID NO: 21) |
| CCAGGAGATTAGGGTCTGT (SEQ ID NO: 2) | GGCTTCAGACCCTAATCTCCTGGGGATTGAGTTTTGAACTCCCAGGAGTTTAGGGTCTG (SEQ ID NO: 12) | ACTCCAGACCCTAAACTCCTGGGAGTTCAAAACTCAATCCCCCAGGAGATTAGGGTCTGA (SEQ ID NO: 22) |
| TGATGGGAATGGAACCTAC (SEQ ID NO: 3) | GGCTTTAGGTTCCATTCCCATCAGGGATTGAGTTTTGAACTCTGATGGGTATGGAACCTA (SEQ ID NO: 13) | ACTCTAGGTTCCATACCCATCAGAGTTCAAAACTCAATCCCTGATGGGAATGGAACCTAA (SEQ ID NO: 23) |
| AAGACCAAGACACACTATC (SEQ ID NO: 4) | GGCTTATAGTGTGTCTTGGTCTTGGGATTGAGTTTTGAACTCAAGACCATGACACACTAT (SEQ ID NO: 14) | ACTCATAGTGTGTCATGGTCTTGAGTTCAAAACTCAATCCCAAGACCAAGACACACTATA (SEQ ID NO: 24) |
| ATGTCCTGCCTGATGGGAA (SEQ ID NO: 5) | GGCTTTCCCATCAGGCAGGACATGGGATTGAGTTTTGAACTCATGTCCTCCCTGATGGGA (SEQ ID NO: 15) | ACTCTCCCATCAGGGAGGACATGAGTTCAAAACTCAATCCCATGTCCTGCCTGATGGGAA (SEQ ID NO: 25) |
| GGTCCTGGATCAACACCCA (SEQ ID NO: 6) | GGCTTGGGTGTTGATCCAGGACCGGGATTGAGTTTTGAACTCGGTCCTGCATCAACACCC (SEQ ID NO: 16) | ACTCGGGTGTTGATGCAGGACCGAGTTCAAAACTCAATCCCGGTCCTGGATCAACACCCA (SEQ ID NO: 26) |
| ATGGTCAGCCCTTCCTGCG (SEQ ID NO: 7) | GGCTTGCAGGAAGGGCTGACCATGGGATTGAGTTTTGAACTCATGGTCACCCCTTCCTGC (SEQ ID NO: 17) | ACTCGCAGGAAGGGGTGACCATGAGTTCAAAACTCAATCCCATGGTCAGCCCTTCCTGCA (SEQ ID NO: 27) |
| GGAACACAGCGGGAATCAC (SEQ ID NO: 8) | GGCTTTGATTCCCGCTGTGTTCCGGGATTGAGTTTTGAACTCGGAACACTGCGGGAATCA (SEQ ID NO: 18) | ACTCTGATTCCCGCAGTGTTCCGAGTTCAAAACTCAATCCCGGAACACAGCGGGAATCAA (SEQ ID NO: 28) |
| TCTGTGCAGTCAGGGTTTC (SEQ ID NO: 9) | GGCTTAAACCCTGACTGCACAGAGGGATTGAGTTTTGAACTCTCTGTGCTGTCAGGGTTT (SEQ ID NO: 19) | ACTCAAACCCTGACAGCACAGAGAGTTCAAAACTCAATCCCTCTGTGCAGTCAGGGTTTA (SEQ ID NO: 29) |
| GAATGGAACCTACCAGACC (SEQ ID NO: 10) | GGCTTGTCTGGTAGGTTCCATTCGGGATTGAGTTTTGAACTCGAATGGATCCTACCAGAC (SEQ ID NO: 20) | ACTCGTCTGGTAGGATCCATTCGAGTTCAAAACTCAATCCCGAATGGAACCTACCAGACA (SEQ ID NO: 30) |

Figure 3:
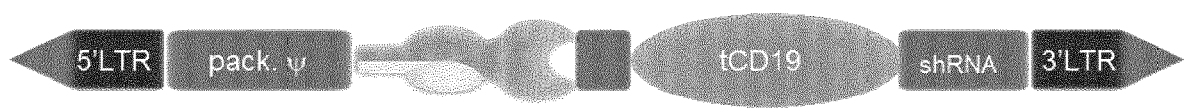
Figure 4:
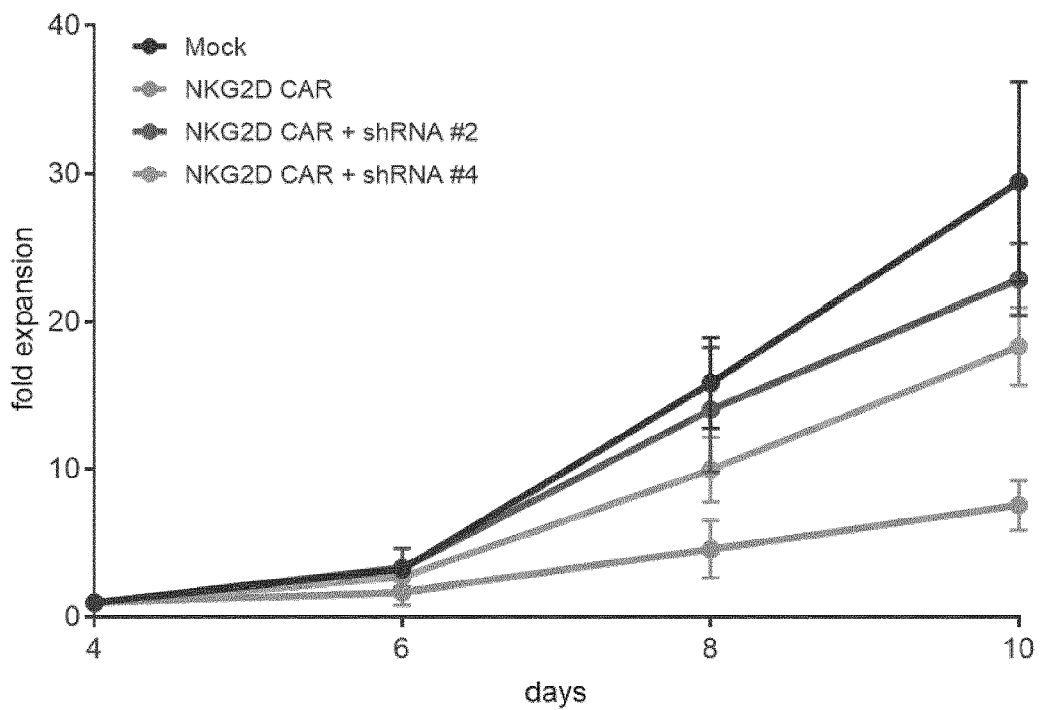
Figure 5:
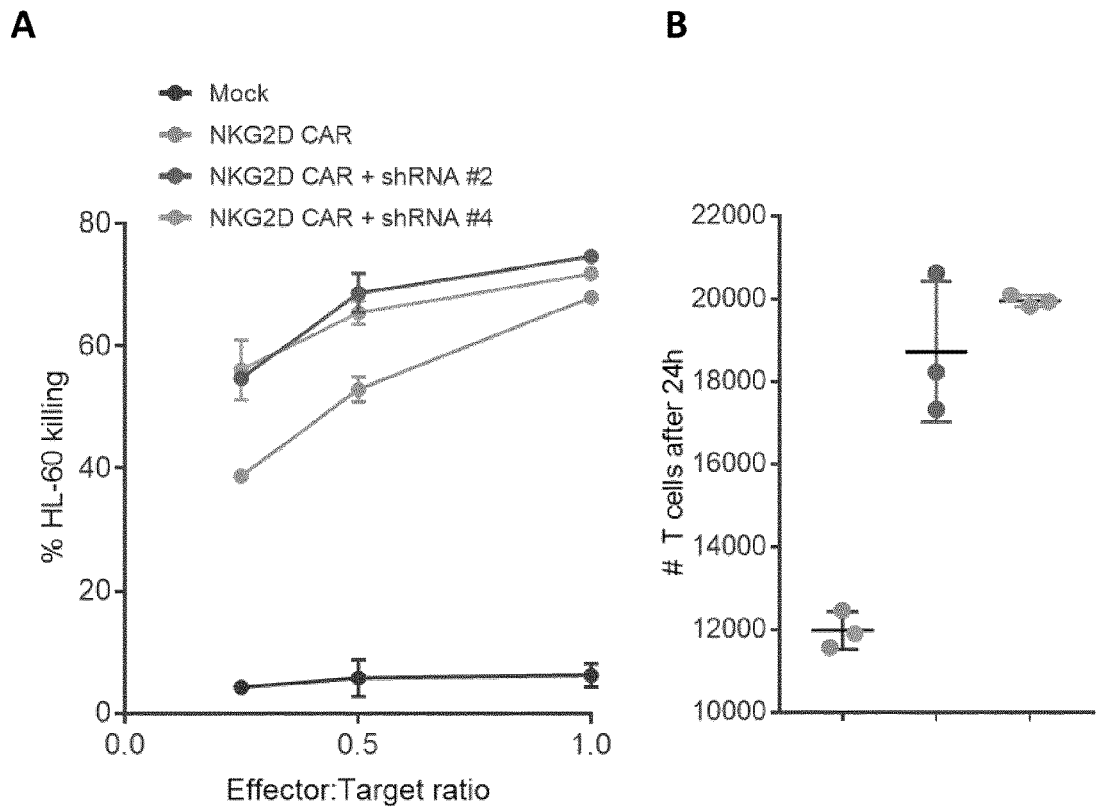

Example 2. Co-Expression of MICA/MICB Targeting shRNA Reduces NK-Receptor Mediated Killing of T cells and improves tumor cell killing in vitro A single retroviral vector encoding the NKG2D CAR and coexpressing the candidate shRNAs identified in Example 1 was engineered, the design is shown in FIG. 3. As the NKG2D CAR confers NK receptor binding specificity to T cells, these cells can mimic the effect of NK clearance (i.e. T cell killing by NK cells). Here, the NKG2D CAR will recognize the NKG2D ligands expressed on T cells, and these cells will be eliminated. This 'self-killing' or killing by identical cells is termed fratricide. We assessed the levels of fratricide in T cells engineered with NKG2D based CAR or T cells co-expressing a shRNA, by means of cell expansion (FIG. 4). Engineering of a single retroviral vector encoding the NKG2D CAR and shRNA generated T cells that had much (targeting sequence CCAGGAGATTAGGGTCTGT) or #4 (targeting sequence AAGACCAAGACACACTATC) improved killing of cancer cells, especially at lower E:T ratios (FIG. 5A). Improved target cell killing was likely due to decreased fratricide (as surrogate marker for decreased NK cell killing) as shRNA expression improved T cell recovery 24h after co-culture (FIG. 5B).

Example 3. Inhibition of NKG2D Ligands Increases Persistence of CAR T Cells, Decrease Tumor Burden and Prolong Survival In Vivo Previous studies have shown a limited engraftment of cells expressing the chimeric NKG2D antigen receptor (also termed NKR2), which may contribute to the transient anti-tumor activity. It was hypothesized that expression of NKG2DL on the CAR-T cells contributed to their reduced engraftment in vivo. To assess this, long-term persistence of CAR T cells was evaluated in NSG mice after a single IV injection.

The global aim of this study was to assess the long-term persistence of Chimeric Antigen Receptor (CAR) T cells in NOD SCID gamma-c-/- (Non-Obese Diabetic Severe Combined ImmunoDeficiency Gamma, NSG) mice after a single intravenous (IV) injection. The persistence in blood of seven different types of T-cell treatments generated from a unique donor (Mock T cells, NKR2 T cells, and NKR2 cells with 5 different shRNAs) was assessed.

NSG mice were irradiated within 24 hours before the IV injection of CAR T cells. These highly immunodeficient mice lack mature T-cells, B-cells, natural killer (NK) cells and are also deficient in multiple cytokine signaling pathways, therefore allowing human cell engraftment.

The persistence of the seven different T-cell treatments was performed in seven groups of four mice (except for the group treated with Mock T cells composed of three mice) treated with a single IV injection of the relevant T cells ($10 \times 10^6$ cells/mouse) within 8 weeks post-injection. One group of 3 mice was receive an injection of vehicle and was used as control, as well as mice injected with Mock T cells.

To assess the long-term persistence of the cells, flow cytometry was performed once a week within 8 weeks to detect human T cell engraftment in blood (1, 6, 13, 20, 27, 34, 41, 48 and 55 days after their IV injection).

Protocol

On Day −1, all the mice were irradiated. The mice were placed in the irradiator X-RAD320. They were irradiated, not anesthetized in their cage, by X-ray at 1.44Gy. The irradiation was performed at 70 cm of the X-ray tube with 0.5Gy/min dose rate and a standard protocol of mice irradiation using the following parameters:

12.5 mA amperage
320 kV voltage.

On Day 0, 2 vials of $50 \times 10^6$ cells/vial of each cell type (Mock T cells, NKR2 T cells, and 5 NKR2 T cells with different shRNAs) were thawed and prepared for injection according to the following protocol:

The X-vivo 15 medium (X-VIVO 15 without Gentamycin and Phenol Red) were preheated at +37° C. in a water bath, The X-vivo 15 medium was supplemented with 1% of Gentamycin concentrated at 50 mg/ml and with 5% of Human male AB Serum heat inactivated (HS) (i.e. 10 ml of Gentamycin and 50 ml of HS were added in a 1000 ml bottle of X-vivo 15 medium), The vials containing frozen cells were transferred in a water bath at +37° C. until a small fragment of ice remains, The vials were decontaminated and transferred under the laminar hood, 1 ml of pure cold HS were added drop by drop in each vial of T cells, 8 ml x the number of thawed vials of pre-warmed complete X-vivo 15 medium were deposited in a 50 ml Falcon tube (16 ml for 2 vials of T cells), The cells were transferred in these 50 ml Falcon tubes and the cryovials were rinsed with 1 ml of cell suspension in order to transfer the totality of T cells, The 50 ml Falcon tubes were centrifuged at 400 g for 5 minutes and then, the supernatants were discarded carefully, 10 ml x the number of thawed vials of complete X-vivo 15 medium were added (20 ml for 2 vials of T cells), The 50 ml Falcon tubes were centrifuged a second time at 400 g for 5 minutes and the supernatants were discarded carefully, Then, the cells of each cell type were resuspended in 600 µl of HBSS (300 µl of HBSS per vial of T cells), An aliquot of 10 µl of cells was diluted in 10 µl of Trypan blue to perform a cell counting and determine the viability using an automatic cell counter, Finally, the cell concentration was adjusted at $50 \times 10^6$ cells/ml in HBSS for IV injection session (200 µl/mouse).

The remaining thawed cells were used to perform the flow cytometry panel validation.

The vehicle, the test and reference items were administered by IV injection in one tail vein with disposable plastic syringes of 1 ml and 26G needles. One syringe per group was used.

Whole blood (WB) of each mouse of all groups (Groups 1 to 8) was collected on Days 1, 6, 13, 20, 27, 34, 41, 48 and 55.

WB was collected by retro-orbital sinus on anesthetized mice (isofluranel-3%), through capillary tubes.

About 150 µl of blood were collected and deposited in micro-centrifuge tubes previously heparinized with 20 µl of heparin.

Animals were euthanized under anesthesia (mix of Isoflurane and oxygen as a carrier gas) by cervical dislocation.

Flow cytometry analyses were performed on 30 samples of WB on Days 1, 6, 13, 20, 27, 34, 41 and 48 and on 29 samples on Day 55.

Human T cells were detected, on WB, after staining, using a combination of mAbs, described in Table 2, containing anti-human CD45 (hCD45), anti-hCD3, anti-hCD314, anti-hCD19, anti-hMICA/B and anti-mouse (mCD45) mAb, in order to exclude murine cells.

Staining was performed according to the following staining protocol:

Red blood cells lysis
Wash cells
Incubate for 10 minutes with mouse Fc Block at 10 µg/ml in the dark at +4° C.
Incubate cells for 20 minutes in the dark at +4° C. with mix of antibodies
Wash cells
Re-suspend cells with 250 µl of Fixative buffer
Acquire 100 000 viable events or totality of tube on BD FACS Canto II flow cytometer.

TABLE 2

Antibodies used for staining

| Description | Supplier | Manufacturer reference | Batch number | Expiry date |
| --- | --- | --- | --- | --- |
| mCD45-BV510 | Ozyme | BLE103138 | B251556 | Nov. 30, 2020 |
| hCD45-BV421 | Ozyme | BLE304032 | B240853 | Jun. 31, 2020 |
| hCD3-PerCP-Cy5.5 | Ozyme | BLE300430 | B240526 | May. 31, 2020 |
| hCD314-PE-Cy7 | Ozyme | BLE320812 | B255992 | Jan. 31, 2020 |
| hCD19-APC-Cy7 | Ozyme | BLE302218 | B252246 | Nov. 30, 2021 |
| hMICA/B-AF488 | Ozyme | BLE320912 | B211982 | Oct. 31, 2020 |

Data

Figure 6:
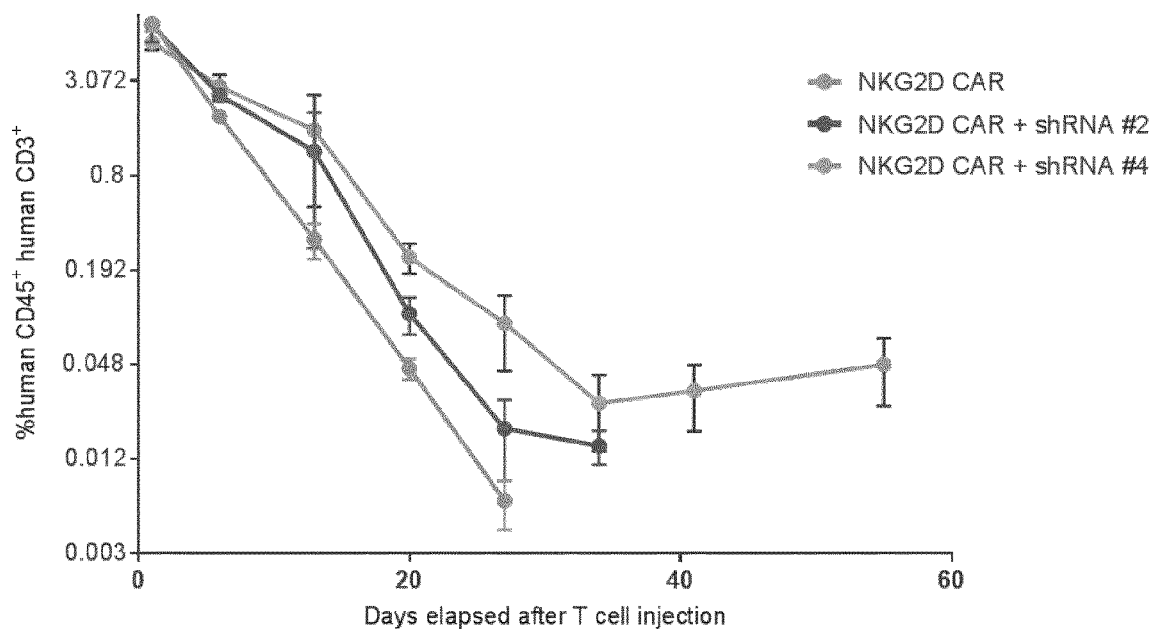

As shown in FIG. 6, NKG2D CAR T cells showed a persistence of 24 days in NSG mice. Coexpression of MICA/B targeting shRNA #2 improved engraftment until day 41. Notably, co-expression of shRNA #4 increased persistency of CAR-T cells in the peripheral blood by at least a factor of 2 until the end of the experiments in all animals. These data demonstrate that inhibition of NKG2D ligands indeed prolongs the persistence of CAR-T cells.

As a next step, it was evaluated if the increased persistence of these CAR-T cells with shRNA leads to an effect on the antitumor activity. To this end, an AML model was used. Acute Myeloid Leukemia (AML) is a hematological cancer that is characterized by the aberrant growth of myeloid progenitor cells. AML is the most common adult acute leukemia and accounts for about 20% of childhood leukemia. Although treatment of AML with cytotoxic chemotherapy achieves high remission rates, about 75% of patients will either not respond to or will relapse after initial therapy, and most patients will die of their disease.

Antitumor efficacy of NKR-2 CAR T cells against AML was assessed in immunodeficient NOD SCID Gamma-c-/- (Non-Obese Diabetic Severe Combined ImmunoDeficiency Gamma, NSG) mice using the THP-1-luc-GFP cell line (acute monocytic leukemia—AML subtype 5) expressing luciferase (luc) and Green Fluorescent Protein (GFP).

The efficacy of NKR-2 (human T cells genetically modified with a retroviral vector coding for a chimeric receptor based on the NKG2D NK receptor generated with a culture process using a blocking mAb) and NKR-2 shRNA T cells (human T cells genetically modified with a retroviral vector coding for a chimeric receptor based on the NKG2D NK receptor and one short hairpin RNA (shRNA) candidate targeting 2 NKG2D ligands, MICA/B (either shRNA #2 or #4)) was assessed in this mouse model.

One reference item (Mock T cells) and vehicle was also injected and used as controls.

The test items, reference item and vehicle were IV administrated 7 days after the tumor cell injection.

The antitumor efficacy of the different CAR-T cells was evaluated by in vivo bioluminescence imaging. A visualization and quantification of the THP-1-luc-GFP cell proliferation and dissemination in the whole animal was performed 8 times within 8 weeks after their IV injection (on Days 4, 8, 13, 22, 29, 36, 43 and 57).

To complete the analysis, flow cytometry was performed on whole blood (WB) 7 times within 8 weeks after tumor cell injection (on Days 8, 13, 22, 29, 36, 43 and 57).

Moreover, the clinical state of each mouse was assessed based on clinical score and body weight (BW) measured 3 times a week in order to detect any abnormal clinical sign(s).

Material and methods is largely as described hereinabove, in this model, 25 mice were IV injected with THP-1-luc-GFP cells ($5 \times 10^6$ cells/mouse) at day 0, followed at day 7 with the injection of the relevant vehicle, mock or CAR T cells.

Figure 7:
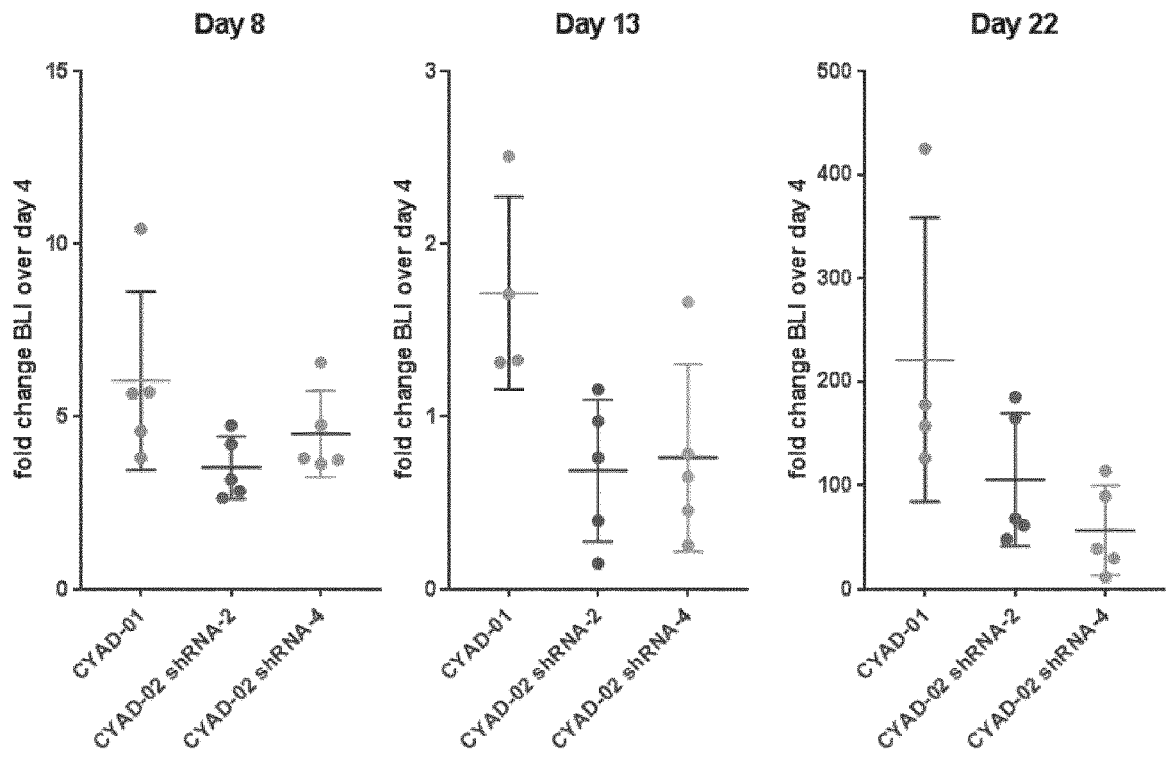
Figure 8:
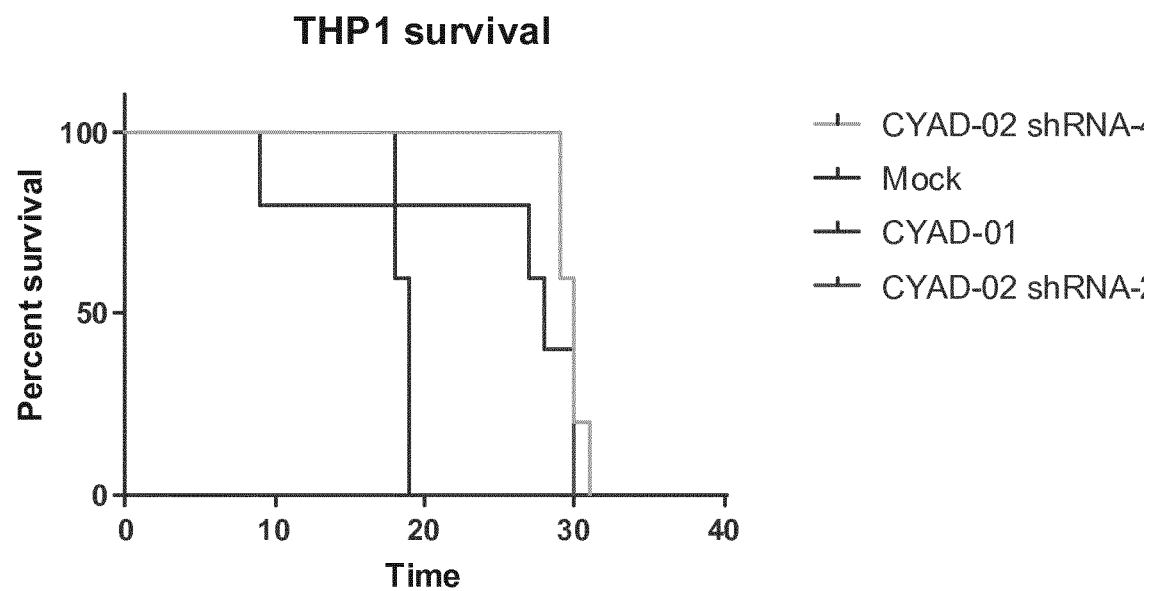

As shown in FIG. 7, NKR2 cells with shRNA against MICA/B appear to slow tumor growth, as evidenced by a reduced tumor burden, particularly in longer timeframes. As shown in FIG. 8, all mice treated with mock cells succumbed to the tumor by day 19. In contrast, mice treated with a CAR survived till day 30. While the addition of shRNA against NKG21D ligands did not extend survival of all mice beyond day 30, mice start to die significantly later than those injected with a CAR alone, indicating an increased benefit on survival of the shRNA. In a less aggressive tumor model or with repeated injections, this benefit may be further improved.

Example 4. Inhibition of NKG2D Ligands with Crispr

Considering the benefit of shRNA against the NKG2D ligands for in vivo applications, it as evaluated whether genetic knockout of NKG2D ligands is also feasible. To this end, CRISPR/Cas was used to knock out MICA and MICB genes (knocking out all 8 genes is technically challenging and commercially not attractive in terms of cost, while a benefit for inhibiting just these two ligands has already been shown).

Figure 9:
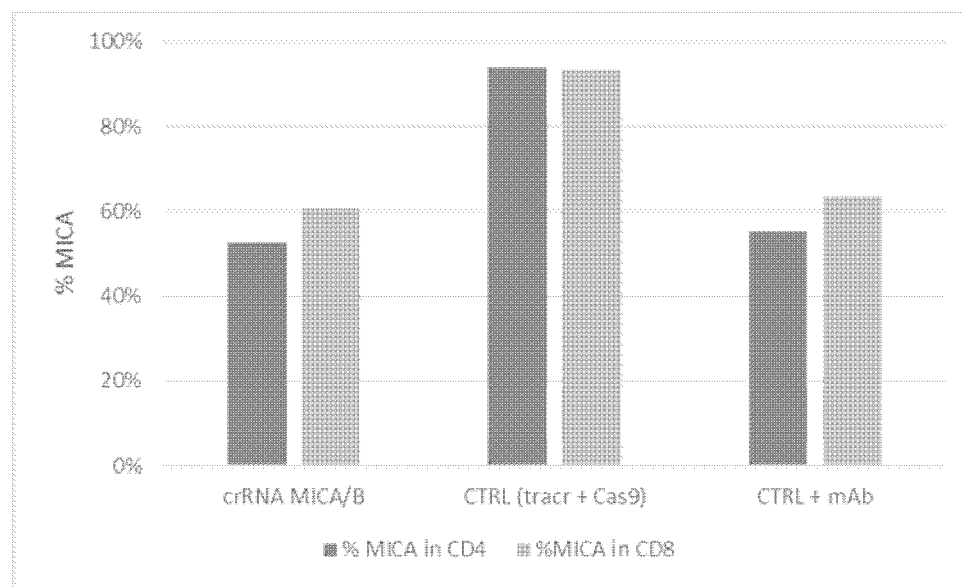
FIG. 9. Inhibition of MICA protein by Crispr/Cas compared to control or shRNA in CD4 and CD8 T cells.

Selected targeting sequences are provided in Table 3, preliminary data showing inhibition of MICA in CD4 and CD8 T cells is shown in FIG. 9. Interestingly, the CRISPR-mediated knockdown indeed reduces MICA protein expression to the same extent as NKR2 cells with a shRNA inhibitor.

TABLE 3

Target sequences of MICA and/or MICB targeting CRISPR/Cas

| Name | Targeting sequence | PAM | Exon |
|---|---|---|---|
| MICA-B-1 (Not targeting one mRNA variant of MICA) | GTCTGAGCTCTGGAGGACTG (SEQ ID NO: 31) | GGG | 4 |
| MICA-B-2 | ACATTCACCATGGGGGCAC (SEQ ID NO : 32) | TGG | 5 |
| MICA-B-3 | AGATACCCCATCCTGACGCC (SEQ ID NO : 33) | AGG | 5 |
| MICA-B-4 (only targeting MICA) | CACGGTGATGTTGCCCTCTG (SEQ ID NO: 34) | AGG on MICA AGA on MICB | 5 |
| MICA-B-5 (Not targeting one mRNA variant of MICA and one of MICB) | GCTCTTCCTCTCCCAAAACC (SEQ ID NO: 35) | TGG (on both genes) | 4 |
| MICA-B-6 (Not targeting one mRNA variant of MICA and one of MICB) | CCCCATCGTAGTAGAAATGC (SEQ ID NO: 36) | TGG on MICA CGG on MICB | 4 |
| MICA-B-7 | GGGCTTCCAGCTTCTATCCC (SEQ ID NO: 37) | CGG | 4 |
| MICA-B-8 | TGGGGGGATGTCCTGCCTGA (SEQ ID NO: 38) | TGG | 4 |
| MICB-9 | CTATGAACGTCACAAATTTC (SEQ ID NO: 39) | TGG | 3 |
| MICA-B-10 (1mismatch in MICB sequence C>A) | CGGGGCCATGGGGCTGGGCC (SEQ ID NO: 40) | CGG | 1 |
| MICA-B-11 (1mismatch in MICB sequence A>G) | CATATCAAGGACCAGAAAGA (SEQ ID NO: 41) | AGG | 2 |
| MICA-B-12 | ATAGTGTGTCTTGGTCTTCA (SEQ ID NO: 42) | TGG | 3 |

CONCLUSION

The above results demonstrate the benefit, both in vitro and in vivo, of reducing or eliminating expression of NK receptor ligands in CAR T cells. Future experiments will focus on expanding the data of CRISPR/Cas mediated knockout, as well as using the technology for other CARs and in different tumor models.

What is claimed is:

1. One or more engineered T cells which comprise:
   (i) an exogenous nucleic acid molecule encoding a chimeric NKG2D receptor; and
   (ii) two or more shRNAs directed against MICA and/or MICB mRNA;
   wherein said two or more shRNAs inhibit the expression of MICA and/or MICB by said engineered T cells, and further wherein said T cells are less sensitive to clearance by NK cells and persist longer in vivo compared to T cells which do not comprise said two or more shRNA inhibitors directed against MICA and/or MICB; and wherein said two or more shRNA inhibitors directed against MICA and/or MICB include a shRNA which targets the nucleic acid of SEQ ID NO: 2 and a shRNA which targets the nucleic acid of SEQ ID NO: 4.

2. A pharmaceutical composition comprising one or more engineered T cells according to claim 1 and a pharmaceutically acceptable carrier.

3. One or more engineered T cells according to claim 1, which comprise one or more CD4+ T cells.

4. One or more engineered T cells according to claim 1, which comprise one or more CD8+ T cells.

5. One or more engineered T cells according to claim 1, which comprise primary human T cells.

6. One or more engineered T cells according to claim 5, which comprise primary human CD4+ T cells.

7. One or more engineered T cells according to claim 5, which comprise primary human CD8+ T cells.

8. One or more engineered T cells which comprise:
   (i) an exogenous nucleic acid molecule encoding a chimeric NKG2D receptor; and
   (ii) one or more shRNAs directed against MICA and/or MICB mRNA;
   wherein said one or more shRNAs inhibit the expression of MICA and/or MICB by said engineered T cells, and further wherein said T cells are less sensitive to clearance by NK cells and persist longer in vivo compared to T cells which do not comprise said one or more shRNA inhibitors directed against MICA and/or MICB; and, wherein said one or more shRNA inhibitors include one or more shRNAs selected from an shRNA which comprises the nucleic acid of SEQ ID NO: 11 and 21; an shRNA which comprises the nucleic acid of SEQ ID NO: 12 and 22; an shRNA which comprises the nucleic acid of SEQ ID NO: 13 and 23; an shRNA which comprises the nucleic acid of SEQ ID NO: 14 and 24; an shRNA which comprises the nucleic acid of SEQ ID NO: 15 and 25; an shRNA which comprises the nucleic acid of SEQ ID NO: 16 and 26; an shRNA which comprises the nucleic acid of SEQ ID NO: 17 and 27; an shRNA which comprises the nucleic acid of SEQ ID NO: 18 and 28; an shRNA which comprises the nucleic acid of SEQ ID NO: 19 and 29; and an shRNA which comprises the nucleic acid of SEQ ID NO: 20 and 30.

9. A pharmaceutical composition comprising one or more engineered T cells according to claim 8 and a pharmaceutically acceptable carrier.

10. One or more engineered T cells according to claim 8, which comprise one or more CD4+ T cells.

11. One or more engineered T cells according to claim 8, which comprise one or more CD8+ T cells.

12. One or more engineered T cells according to claim 8, which comprise primary human T cells.

13. One or more engineered T cells according to claim 8, which comprise primary human CD4+ T cells.

14. One or more engineered T cells according to claim 8, which comprise primary human CD8+ T cells.

* * * * *